(12) United States Patent
Treacy

(10) Patent No.: US 6,506,556 B2
(45) Date of Patent: Jan. 14, 2003

(54) SYNERGISTIC INSECT CONTROL

(75) Inventor: Michael Frank Treacy, Newton, PA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/755,923

(22) Filed: Jan. 5, 2001

(65) Prior Publication Data

US 2001/0041175 A1 Nov. 15, 2001

Related U.S. Application Data
(60) Provisional application No. 60/175,101, filed on Jan. 7, 2000.

(51) Int. Cl.$^7$ ............................ C12Q 1/70; C12N 15/00
(52) U.S. Cl. ......................... 435/5; 435/320.1; 435/325; 800/302; 424/93.6
(58) Field of Search ........................ 435/5, 320.1, 325; 800/302; 424/93.6

(56) References Cited

U.S. PATENT DOCUMENTS 5,858,353 A  *  1/1999  Miller et al.

FOREIGN PATENT DOCUMENTS

WO     WO 96/03048     *  7/1995

OTHER PUBLICATIONS

All, J. N. and Treacy, M. F., 1997 Proceedings Beltwide Cotton Conference, p 1294.*
Benedict, J. H., et al., Journal of Economic Entomology, vol. 89 (1996), pp 230–238.*
Colby, S. R., Weeds, 1967 (15), pp 20–22.*

* cited by examiner

Primary Examiner—Ali R. Salimi
(74) Attorney, Agent, or Firm—Keil & Weinkauf

(57) ABSTRACT

There is provided a method for the synergistic control of insects which comprises applying to the locus of a transgenic crop which produces an insect toxin a synergistically effective amount of a recombinant insect virus containing a vector which is highly virulent to said insect.

10 Claims, No Drawings

SYNERGISTIC INSECT CONTROL

This application claims priority from copending provisional application(s) Ser. No. 60/175,101 filed on Jan. 7, 2000.

BACKGROUND OF THE INVENTION

Control of insect pests by chemical means has long been a useful method to protect crops from damage caused by insect-attack and infestation. More recently, methods to control insect crop damage have been introduced which are specific to the target insect and avoid environmental and ecological compromise associated with traditional pesticide usage. One of these methods employs a genetically modified crop which produces insect-specific toxins, e.g., the Cry toxin from *Bacillus thuringiensis*. However, the *B. thuringiensis*-Cry-toxin-expressing crop may exhibit varying degrees of protection from an array of lepidopteran pest species. For example, CryIA(c)-expressing cotton varieties are highly resistant to tobacco budworm, *Heliothis virescens*, but only moderately resistant to cotton bollworm *Helicoverpa zea* (J. H. Benedict et al., 1996, Journal of Economic Entomology, Vol. 89(1), p. 230).

Another such method of insect control is the application of biological agents such as a nucleopolyhedrosis virus (NPV)(U.S. Pat. No. 4,668,511), or recombinant nucleopolyhedrosis virus (rNPV) (U.S. Pat. No. 5,662,897 and U.S. Pat. No. 5,858,353). However, NPV and rNPV may vary in the level of virulence/potency against various insect species, depending upon the host range of the viral vectoring agent and the potency of the toxin encoded by the inserted gene. For example, the insect species *Helicoverpa zea* is highly susceptible to the NPV and rNPV designated HZNPV and HzAaIT, respectively, but only moderately susceptible to the *Autographa californica* NPV (AcNPV) or its rNVP, AcAaIT (Treacy et al., 1999, Proceedings Beltwide Cotton Conf., pp. 1076–1083). Although the combination of applying a recombinant nucleopolyhedrosis virus which contains a vector which is moderately virulent to the target insect species to a transgenic crop line has been described, (All and Treacy, 1997, Proceedings Beltwide Cotton Conf. p. 1294), neither the transgenic crop nor the rNPV agent, alone or in combination, provided the level of insect control needed to prevent crop loss on a commercial basis.

Therefore, it is an object of this invention to provide a method of synergistic insect control useful for preventing crop damage and economic loss caused thereby.

It is another object of this invention to provide a method for the enhanced protection of a transgenic crop from the devastation and damage caused by insect attack and infestation.

It is a feature of this invention that the synergistic insect control and crop protection methods provided are specific to the target insect species and demonstrate enhanced environmental and ecological compatability, while providing commercially acceptable levels of insect control and crop protection.

Other objects and features of the invention will be apparent to those skilled in the art from the following description and the appended claims.

SUMMARY OF THE INVENTION

The present invention provides a method for synergistic insect control which comprises applying to the locus of a transgenic crop a synergistically effective amount of a recombinant insect virus containing a vector which is highly virulent to said insect.

Further provided is a method for the enhanced protection of a transgenic crop from damage caused by insect attack and infestation.

DETAILED DESCRIPTION OF THE INVENTION

Although chemical pest control has been an effective means of controlling important agronomic insect pests, more target insect-specific methods of control have been introduced. Among these insect-specific methods are the use of a transgenic crop which has been genetically altered to produce an insect toxin such as *Bacillus thuringiensis* (Bt) or the use of a naturally occurring virus such as the nucleopolyhedrosis virus (NPV) or recombinant NPV (rNPV). However, the transgenic crop which produces a Bt toxin may exhibit a less than satisfactory degree of protection from the targeted insect. Similarly, naturally occurring and recombinant insect viruses often demonstrate varying degrees of efficacy when used as the sole method of insect control.

Although the use of a combination of an rNPV which contains a vector which is moderately virulent to the target insect species and a transgenic crop has been described, the results achieved were not satisfactory for commercial insect control when said rNPV was applied alone or when said rNPV was applied in combination with a transgenic crop genetically altered to produce an insect toxin.

Surprisingly, it has now been found that the application of a recombinant insect virus which contains a vector which is highly virulent to the target insect species to a transgenic crop, preferably a transgenic crop which has been genetically altered to produce an insect toxin (insecticide), demonstrates a significant synergistic effect (i.e. the resultant insect control is much greater than that which could be predicted from the insect control of the virulent recombinant insect virus when used alone or from the insect control of the transgenic crop when used alone). This synergistic effect enables a commercially useful level of insect control via a non-chemical biological means. Further, the synergistic insect control method of the invention allows for effective resistance management compatable with sustainable agriculture practices which are environmentally and ecologically sound.

In accordance with the method of the invention, the application of a synergistically effective amount of a recombinant insect virus, preferably a recombinant nucleopolyhedrosis virus (rNPV), containing a vector which is highly virulent to the target insect species to a transgenic crop variety, preferably a transgenic crop which is genetically altered to produce an insect toxin, provides synergistic control of the insect pest. That is, the application of the virulent recombinant insect virus to the transgenic crop results in a combination of insecticidal components which produces a greater insecticidal effect than that which would be expected from the individual insecticidal components employed individually (synergistic effect).

Recombinant insect viruses containing a highly virulent vector which are suitable for use in the method of invention include rNPVs such as HzNPV, HzAaIT, EGTdel, or a combination thereof. Transgenic crops which produce an insect toxin suitable for use in the method of invention include Bt expressing lines of maize and cotton(BTK lines), such as NuCotn 33B™, a transgenic cotton variety derived from Deltapine DP5415™ by the Bollgard™ transformation event, or transgenic maize varieties such as those which express the MON 810™ transformation event (YieldGard™, Monsanto Co.).

In actual practice, the virulent recombinant insect virus may be applied in the form of a formulated composition, such as a wettable powder, to the locus, foliage or stems, preferably the foliage, of a transgenic crop, particularly a transgenic crop which has been genetically altered to produce an insect toxin. A preferred formulation is that described in co-pending U.S. patent application Ser. No. 09/094,279, filed Jun. 9, 1998, incorporated herein by reference thereto.

The synergistically effective amount of the virulent recombinant insect virus may vary according to prevailing conditions such as the degree of insect resistance of the transgenic crop, the application timing, the weather conditions, the mode of application, the density of the insect population, the target crop species, the target insect species, and the like. In general, synergistic insect control may be obtained when the virulent recombinant insect virus is applied to the transgenic crop at rates of about $1 \times 10^{10}$ occlusion bodies per hectare (OB/ha) to about $1 \times 10^{13}$ OB/ha, preferably about $5 \times 10^{10}$ OB/ha to about $12 \times 10^{11}$ OB/ha.

In order to facilitate a further understanding of the invention, the following examples are presented primarily for the purpose of illustrating more specific details thereof. The invention should not be deemed limited thereby except as defined in the claims.

In the following examples, synergism for two-way insecticidal combinations is determined by the Colby method (Colby, S. R., *Weeds*, 1967 (15), pp.20–22), i.e. the expected (or predicted) results (percentage of insects eliminated) of the combination is calculated by taking the sum of the results for each insecticide component applied alone and subtracting the product of these two results divided by 100. This is illustrated mathematically below, wherein a two-way combination is composed of component X plus component Y.

$$(X + Y) - \frac{XY}{100} = \text{Expected results}$$

If the actual observed results are greater than the expected results calcualted from the formula, synergy exists.

In the present invention, the percent insect control (no external insecticide applied) exhibited by a transgenic crop of this invention relative to a closely related control crop could be represented by X; and the percent control of a recombinant insect virus of the invention when used on the control crop could be represented by Y. The foregoing Colby formula can be used to calculate the expected percent control for the combination of the virus and the transgenic crop. If the observed results (actual percent control) of the combination of the transgenic crop treated with the virus is greater than the calculated expected results, then the combination is synergistic.

EXAMPLE 1

Evaluation of the Synergistic Insecticidal Effect of A Virulent Recombinant Insect Virus Applied to A Transgenic Crop In this evaluation a test system is used which approximates foliar-spray and plant architecture parameters typically encountered in cotton field scenarios. The insecticidal effect of (a) the application of a wettable powder (WP) formulation of HzAaIT at rates of $5 \times 10^{11}$ OB/ha and $12 \times 10^{11}$ OB/ha and (b) the *Bacillus thuringiensis* CryIA(c)-expressing cotton variety, 'NuCotn 33B', is evaluated and compared to combinations using a conventional cotton variety, 'Deltapine DP54151'.

Plants are grown from seed in 3.8-liter plastic pots which are filled with commercial potting soil. For comparison purposes, conventional Deltapine DP5415 cotton is included in the study. Viral applications to cotton are initiated about 1.5 months after the cotton planting date. Potted plants are sprayed in an enclosed chamber which is equipped with an overhead, rotary hydraulic boom. The boom is fitted with three hollow cone nozzles (TX3, Spraying Systems, Wheaton, Ill.; one nozzle is mounted to apply spray directly over plants and two nozzles are mounted on drop tubes angled at about 45° to spray sides of plants. The sprayer is calibrated to deliver 189 liters/ha at 3.5 $kg/cm^2$; compressed air is used as the spray propellant. The formulated rNPV insecticide is suspended in dechlorinated water, along with the gustatory stimulant, Coax™ (CCT Corp., Carlsbad, Calif.), at 3.5 L/ha. Plants are sprayed three times at 7-day intervals. Potted cotton plants are arranged in a completely randomized design with four replications on table-tops which are flooded with water to a depth of about 2 cm to prevent larval migration between plants. Two plants per treatment are given replicate doses, with replicate subsamples taken from separate tests. Environmental parameters for the greenhouse during the course of the study are programmed for an average daily low temperature of about 27° C. and an average daily high of about 32° C.

The plants are infested with laboratory-reared, neonate *H. zea* at about 1 hr after each spray session. With the use of a small paint brush, larvae are placed on leaves and squares throughout the upper portion of each cotton plant. A total of 30 freshly hatched larvae are placed on each plant following each of the three spray sessions. Artificial placement of larvae on plants is designed to approximate natural distribution of eggs and small larvae of this pest species on cotton (Farrar & Bradley, 1985, *Environ. Entomol.*). Efficacy of treatments applied to cotton is determined 7 days after the third application session by recording numbers of damaged and non-damaged squares per plant. Significant differences among treatments in injury to cotton by *H. zea* are determined by analysis of variance (ANOVA, SAS Institute, 1989). Treatment means are separated by Duncan's multiple range test (DMRT; SAS Institute, 1989).

Means followed by a common letter are not significantly different as determined by Duncan's multiple range test ($P<0.05$; F [df 5, 18]=16.9); percentile data are arcsine transformed for analysis.

Numbers of damaged and non-damaged squares affixed to each plant are assessed 7 days after the final application/infestation session (7DA3T=7 Days After $3^{rd}$ Treatment application)

RESULTS

In this greenhouse study, weekly infestations of *H. zea* larvae caused significantly more injury to untreated DPS41S cotton (susceptible) than to untreated NuCotn 33B (resistant),(53.0% and 20.8t damaged squares, respectively). Foliar applications of HzAaIT at rates of $5 \times 10^{11}$ OB/ha and $12 \times 10^{11}$ OB/ha significantly reduced insect damage on both varieties of cotton. The susceptible plant variety DP5415 when treated with HzAaIT at rates of $5 \times 10^{11}$ OB/ha and $12 \times 10^{11}$ OB/ha, gave an average of 27.6% and 23.9% damaged squares, respectively. The resistant plant variety NuCotn33B when treated with HzAaIT at rates of $5 \times 10^{11}$ OB/ha and 12×10$^{11}$ OB/ha gave an average of 8.8% and 5.0% damaged squares, respectively. The data are shown on Table I.

As can be seen from the data on Table I, foliar application of a virulent recombinant insect virus (HzAaIT) to a transgenic crop (NuCotn33) at a rate of 12×10" OB/ha reduces the insect damage by 4.2-fold as compared to the insect damage to the untreated transgenic crop, whereas the application of said virulent recombinant insect virus to a susceptible crop (DP5415) at a rate of 12×10" OB/ha reduces the insect damage by only 2.2-fold as compared to the untreated susceptible crop. Therefore, the combination of the application of a virulent recombinant insect virus to a transgenic crop gives approximately 2-fold the reduction of insect damage than that which can be expected from either the application of the virulent recombinant insect virus alone or from the use of a transgenic crop alone.

TABLE I

Control of Cotton Bollworm, *Helicoverpa Zea*, on Conventional and Transgenic Cotton Varieties with Foliar Applications of the Recombinant Nucleopolyhedrovirus HzNPV (Egtdel)/DA26-ADK-AaIT (HzAaIT)

| Cotton variety & foliar treatment | Mean % squares damaged (±SD) 7DA3T | % Control² Observed | Expected |
|---|---|---|---|
| DP5415 | | | |
| HzAaIT 5 × 10$^{11}$ OB/ha | 27.6 b¹ (±7.5) | 47.9 | NA |
| HzAaIT 12 × 10$^{11}$ OB/ha | 23.9 b (±6.8) | 54.9 | NA |
| Non-treated | 53.0 a (±9.4) | NA | NA |
| NuCotn 33B | | | |
| HzAaIT 5 × 10$^{11}$ OB/ha | 8.8 c (±5.6) | 83.4* | 79.6 |
| HzAaIT 12 × 10$^{11}$ OB/ha | 5.0 c (±3.4) | 90.6* | 82.3 |
| Non-sprayed | 20.8 b (±10.4) | 60.8 | NA |

¹Means followed by a common letter are not significantly different as determined by Duncan's multiple range test (P < 0.05; F [df 5, 18] = 16.9); percentile data were arcsine transformed for analysis.

TABLE I-continued

Control of Cotton Bollworm, *Helicoverpa Zea*, on Conventional and Transgenic Cotton Varieties with Foliar Applications of the Recombinant Nucleopolyhedrovirus HzNPV (Egtdel)/DA26-ADK-AaIT (HzAaIT)

| Cotton variety & foliar treatment | Mean % squares damaged (±SD) 7DA3T | % Control² Observed | Expected |
|---|---|---|---|

$$^2\text{control} = \left[\frac{\%\ \text{dam. sq. (non-treated)} - \%\ \text{dam. sq. (treated)}}{\%\ \text{dam. sq. (non-treated)}}\right] \times 100$$

*Synergism = Observed > Expected

I claim:

1. A method for synergistic control of an insect which comprises applying to the locus, foliage or stem of a transgenic crop which produces an insect toxin a synergistically effective amount of a recombinant insect virus containing a vector which is highly virulent to said insect, wherein said recombinant virus is HzNPV, HzAaIT, ETGdel or a combination thereof and wherein said transgenic crop is a crop plant which has been genetically altered to express *Bacillus thuringiensis* toxin.

2. The method according to claim 1 wherein said transgenic crop is maize.

3. The method according to claim 1 wherein said transgenic crop is cotton.

4. The method according to claim 3 wherein said crop is NuCotn 33B.

5. The method according to claim 1 where the synergistically effecting amount of said recombinant insect virus is about 1×10$^{10}$ OB/ha to about 1×10$^{13}$ OB/ha.

6. The method according to claim 5 wherein the insect is Lepidoptera.

7. The method according to claim 6 wherein the insect is *Helicoverpa zea*.

8. The method of claim 3 wherein the recombinant virus is HzAaIT.

9. The method of claim 4 wherein the recombinant virus is HzAaIT.

10. The method of claim 9 wherein the insect is *Helicoverpa zea*.

* * * * *